United States Patent [19]

Stone

[11] 4,069,333

[45] Jan. 17, 1978

[54] ANTI-HYPERTENSIVE COMPOSITIONS

[75] Inventor: Clement A. Stone, Blue Bell, Pa.

[73] Assignee: Merck & Co., Inc., Rahway, N.J.

[21] Appl. No.: 766,636

[22] Filed: Feb. 8, 1977

Related U.S. Application Data

[62] Division of Ser. No. 657,824, Feb. 13, 1976.

[51] Int. Cl.² .................. A61K 31/42; A61K 31/24;
  A61K 31/195
[52] U.S. Cl. .................................. 424/272; 424/309;
  424/319
[58] Field of Search ........................................ 424/272

[56] References Cited

U.S. PATENT DOCUMENTS 3,839,585   10/1974   Lotti et al. ............................ 424/319

OTHER PUBLICATIONS

Zinner et al. — Chem. Abst., vol. 66 (1967), p. 55426m.

*Primary Examiner*—Sam Rosen
*Attorney, Agent, or Firm*—Daniel T. Szura; Rudolph J. Anderson, Jr.

[57] ABSTRACT

Novel pharmaceutical compositions comprising hydrazino-phenylpropionic acid decarboxylase inhibitors and certain benzimidazole and benzoxazole alanines are disclosed. The compositions have enhanced hypotensive activity.

5 Claims, No Drawings

ANTI-HYPERTENSIVE COMPOSITIONS

This is a division of application Ser. No. 657,824 filed Feb. 13, 1976.

BACKGROUND OF THE INVENTION

The invention is directed to pharmaceutical compositions having antihypertensive properties. The active ingredients of the compositions are a hydrazino phenylpropionic acid decarboxylase inhibitor and certain aryl (benzimidazole and benzoxazole)alanines.

The hydrazine phenylpropionic acid decarboxylase inhibitors are disclosed in U.S. Pat. Nos. 3,462,536; 3,781,415 and 3,830,827. Certain benzimidazole alanines are disclosed in J. Med. Chem. 13, 741–742 (1970), J. Med. Chem. 17, 1223–1225 (1974) and Abstract No. 964 of the Fifth International Congress On Pharmacology, July 23–28 (1972). The combination of certain hydrazino phenyl propionic acid decarboxylase inhibitors with certain hydroxyphenyl alanines and reserpine is disclosed in Canadian Pat. No. 737,907, U.S. Pat Nos. 3,462,536 and 3,839,585.

It has now been discovered that novel combinations of benzimidazol- and benzoxazole alanines with hydrazino phenylpropionic acid decarboxylase inhibitors have enhanced antihypertensive activity.

SUMMARY OF THE INVENTION

Novel pharmaceutical compositions comprising certain benzimidazole and benzoxazole alanines and D,L- and L- hydrazino phenylpropionic acid decarboxylase inhibitors and method for treating hypertensive animals.

DESCRIPTION OF PREFERRED EMBODIMENTS

An embodiment of the present invention is a pharmaceutical composition comprising (A) a decarboxylase inhibitor compound having the formula:

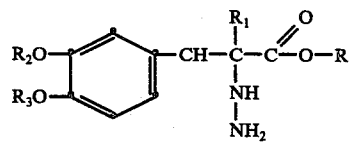

wherein R, $R_1$, $R_2$ and $R_3$ are independently selected from hydrogen and $C_1$–$C_4$ alkyl, and pharmaceutically acceptable salts thereof and (B) an aryl alanine selected from compounds having the formula (1)

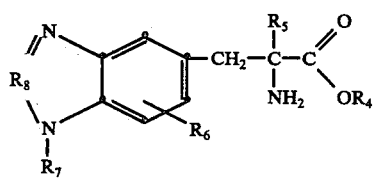

wherein $R_4$, $R_5$, $R_7$ and $R_8$ are independently selected from hydrogen and $C_1$–$C_4$ alkyl, $R_6$ is selected from the group consisting of hydrogen, halogen (e.g. Cl, Br, I or F). —OH and $C_1$–$C_4$ alkyl and pharmaceutically acceptable salts thereof. and (2)

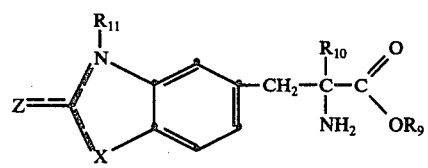

wherein $R_9$, $R_{10}$ and $R_{11}$ are independently selected from hydrogen and $C_1$–$C_4$ alkyl, X is —O— or

wherein $R_{12}$ is hydrogen or $C_1$–$C_4$ alkyl and Z is = O or —O—$R_{13}$ wherein $R_{13}$ is selected from hydrogen or $C_1$–$C_4$ alkyl and pharmaceutically acceptable salts thereof.

The term decarboxylase inhibitor includes the racemic mixture (D,L) and the L- isomer, unless otherwise indicated.

Preferred decarboxylase inhibitors of Formula I are those wherein $R_1$ is selected from hydrogen and methyl, $R_2$, $R_3$ and R are hydrogen. The decarboxylase inhibitor wherein R, $R_2$ and $R_3$ are hydrogen and $R_1$ is methyl is especially preferred. Particular preferred decarboxylase inhibitors are the L-isomers, substantially free of the D-isomer. The most preferred decarboxylase inhibitor is L-isomer of α-hydrazino-β-3,4-dihydroxyphenylpropionic acid and its pharmaceutically acceptable salts. The hydrate of this most preferred decarboxylase inhibitor is also know as carbidopa.

Examples of useful decarboxylase inhibitors are
α-hydrazino-β-3,4-dimethoxyphenylpropionic acid,
α-hydrazino-β-3,4-di-tert-butoxyphenylpropionic acid,
α-hydrazino-β-3,4-dihydroxyphenylpropionic acid methyl ester,
α-hydrazino-β-3,4-diisopropoxyphenylpropionic acid tert.-butyl ester,
and the like.

Preferred compounds of Formula II are those wherein $R_6$ is hydrogen. The more preferred compounds are those wherein $R_4$, $R_6$, $R_7$ and $R_8$ are hydrogen. Especially preferred compounds are the more preferred compounds wherein $R_5$ is hydrogen or methyl and the pharmaceutically acceptable salts.

Examples of useful compounds of Formulae II are
3-(1,2-dimethylbenzimidazol-5-yl)-2-n-butylalanine,
3-(2-butylbenzimidazol-5-yl)-2-isopropylalanine,
3-(1-butylbenzimidazol-5-yl)-2-ethylalanine,
3-(1-ethyl-6-chlorobenzimidazol-5-yl)-2-alanine,
3-(4-hydroxybenzimidazol-5yl)-2-methylalanine,
3-(6-methylbenzimidazol-5-yl)-2-ethylalanine methyl ester,
4-(2-ethylbenzimidazol-5-yl)-2-propylalanine butyl ester,
and the like.

Preferred compounds of Formula III include oxo compounds having the formula

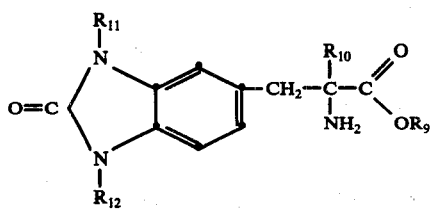

as well as ether compounds of Formula IVa or IVb:

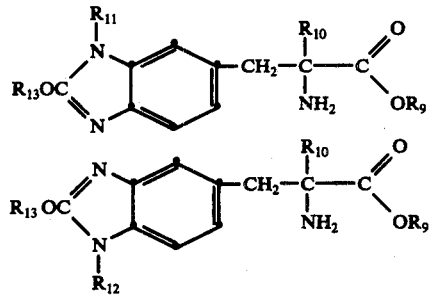

It will be understood by those skilled in the art that the compound of the foregoing general Formula IV wherein Z is O= and $R_{11}$ or $R_{12}$ is hydrogen exists in a tautomeric equilibrium with the corresponding 2-hydroxybenzimidazoles:

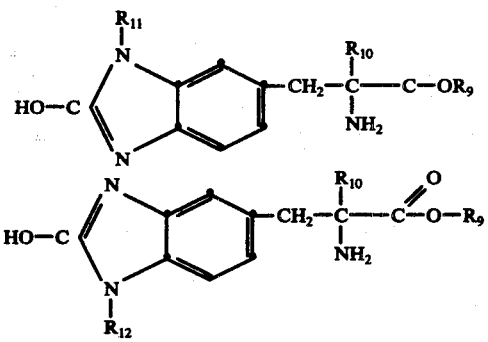

The compounds of the foregoing general Formulae IVa and IVb wherein Z is $R_{13}O$— are alkyl ethers of the 2-hydroxy tautomers of Formula IVc and IVd.

The Formula III compounds also include the benzoxazolones having the formula:

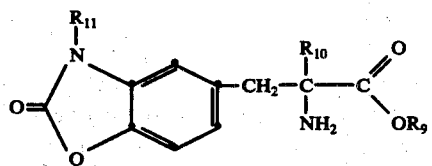

the tautomer thereof, when $R_{11}$ is hydrogen, having the formula:

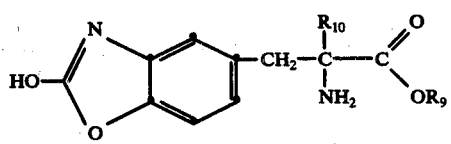

and the alkyl ether of Va having the formula:

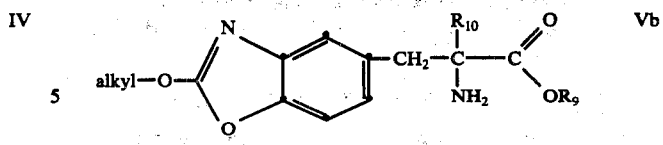

Useful compounds of Formula II and III include
3-(Benzoxazol-2-one-5yl)-alanine,
3-(Benzimidazol-2-one-5yl)-alanine,
3-(Benzimidazol-2-one-5-yl)-2-methylalanine,
2-Amino-3-(3-methyl-2-oxo-1H-benzimidazol-5-yl)-propionic acid,
2-Amino-2-methyl-3-(3-methyl-2-oxo-1H-benzimidazol-5-yl)-propionic acid,
2-Amino-3-(3-methyl-2-oxo-1H-benzimidazol-6-yl)-propionic acid,
2-Amino-2-methyl-3-(3-methyl-2-oxo-1H-benzimidazol-6-yl)-propionic acid,
2-Amino-3-(1,3-dimethyl-2-oxo-2H-benzimidazol-5-yl)-propionic acid,
2-Amino-2-methyl-3-(1,3-dimethyl-2-oxo-2H-benzimidazol-5-yl)-propionic acid,
2-Amino-3-(2-ethoxybenzimidazol-5-yl)-propionic acid,
2-Amino-3-(1-methyl-2-ethoxybenzimidazol-6-yl)-propionic acid,
2-Amino-3-(1-methyl-2-ethoxybenzimidazol-5-yl)propionic acid,
2-Amino-2-methyl-3-(2-ethoxybenzimidazol-5-yl)propionic acid,
2-Amino-2-methyl-3-(1-methyl-2-ethoxybenzimidazol-5-yl)propionic acid,
2-Amino-2-methyl-3-(1-methyl-2-ethoxybenzimidazol-6-yl-acid,
D,L-3-(Benzimidazol-2-one-5-yl)-2-methylalanine methyl ester
and the like.

The compounds having Formula I may be prepared by the reaction of phosgene with a diamino compound of the formula:

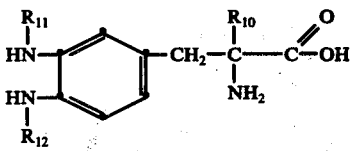

wherein $R_{10}$ is hydrogen or alkyl of from 1 to 4 carbon atoms.

This reaction takes place under conventional conditions at temperatures of from about 10° to about 30° C., preferably at about room temperature, over a period of from a few minutes to several hours, preferably for about 0.5 to about 2 hours.

The diamino compound of Formula V may be prepared by hydrogenating a compound of the formula

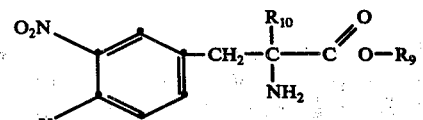

wherein X is nitro or amino. The hydrogenation preferably is carried out catalytically under conventional conditions, by using a palladium/carbon catalyst at about room temperature at a pressure of about 2.5 atmospheres.

The alkyl ethers of Formula IVa and IVb may be prepared by reacting a diamino compound of Formula V with iminocarbonic acid diethylester following the procedure of Sandmeyer, Ber., 19, 2650 (1896) which disclosure is hereby incorporated by reference.

The arylalanines of the present composition have an asymmetric carbon atom and are optically active. Thus, the arylalanines encompass the mixtures of D and L isomers, including the racemic mixture (D, L) as well as the individual enantiomorphs, i.e. the D-isomer or the L-isomer. These isomers may also be designated by the terminology S, (sinister) and R (rectus). The L-isomer is generally the more preferred form of the arylalanine.

The pharmaceutically acceptable salts of the compounds of Formula I, II and III include salts with organic and inorganic acids as well as the ammonium salts and metal salts such as those of Na, K, Ca and the like. Useful organic acids are the $C_2$–$C_{24}$ carboxylic acids exemplified by acetic acid, oxalic acid, citric acid, isethionic acid, pamoic acid, maleic acid, succinic acid, pivalic acid and the like. Useful inorganic acids are the hydrohalides e.g. HCl, HI, and HBr, sulfuric acid and phosphoric acids e.g. $H_3PO_4$.

The compounds of the present compositions also occur as hydrates and these are also included.

The following examples illustrate preparation of compounds of Formula III. All temperatures are in degrees centigrade.

EXAMPLE 1

DL-3-(Benzimidazol-2-one-5-yl)-2-methylalanine Hydrochloride

A mixture of DL-methyl N-acetyl-3-(3-nitro-4-acetamidophenyl)-2-methylalanate (0.85 g., 2.5 mmole) and 4N HCl (50ml.) is held at reflux for 2 hours. The resulting red-orange solution is cooled and then reduced with hydrogen (initial pressure 35 psi) on 10% palladium on charcoal catalyst (300 mg.) at room temperature overnight. The mixture is then filtered under a nitrogen atmosphere through a bed of diatomaceous earth by suction and phosgene is bubbled (approximately 60 ml/min.) through the filtrate for 1 hour. The white precipitate which develops is collected: 0.4 g., 1.5 mmole, 59%. Two recrystallizations from $H_2O$ provide an analytical sample; m.p. 333° (decomp) of D,L-3-(benzimidazol-2-one-5-yl)-2-methylalanine hydrochloride.

EXAMPLE 2

L-3(Benzimidazol-2-one-5-yl)-2-methylalanine Hydrochloride

Following the procedure for the production of the racemic mixture in Example 1, L-methyl-N-acetyl-3-(3-nitro-4-acetamidophenyl)-2-methylalanate is hydrolyzed and then cyclized with phosgene to give Example 2 title compound: m.p. 303° (decomp).

EXAMPLE 3

DL-3-(benzimidazol-2-one-5-yl)alanine Hydrochloride

Following the procedure for the production of the racemic mixture in Example 1, diethyl 2-(3-nitro-4-acetamidobenzyl)-2-acetaminomalonate is hydrolyzed and cyclized with phosgene to produce pure Example 3 title compound in 54% yield: m.p. 259° (decomp).

EXAMPLE 4

2-Amino-3-(3-methyl-2-oxo-1H-benzimidazol-5-yl)propionic Acid Hydrochloride

A. Diethyl-2-(3-nitro-4-acetamidobenzyl)-2-acetamidomalonate

A mixture of diethyl-4-aminobenzylacetamidomalonate (85 g., 0.254 M), glacial acetic acid (85 ml.) acetic anhydride (85 ml.), and zinc dust (2.2 g.) is refluxed for 30 minutes. While still hot, the mixture is poured into stirred ice water. The resulting precipitate is filtered, washed with water and recrystallized from ethanol:water to yield 91.2 g. (96%) of diethyl-4-acetylaminobenzylacetamidomalonate, m.p. 173°–174°.

To a mixture of diethyl-4-acetylaminobenzylacetamidomalonate (15 g., 0.04 M) suspended in acetic anhydride (49 ml.) 70% nitric acid (17 ml.) is added slowly with stirring while maintaining the reaction temperature at 35°–40°. After the addition is complete, the yellow solution is maintained at 40° for 2 hours, then poured into 600 ml. of stirred ice water. The resulting precipitate is filtered rapidly and washed with water. Recrystallization from ethanol:water yields 14.4 g (85%) of diethyl-2-(3-nitro-4-acetamidobenzyl)-2-acetamidomalonate, m.p. 172°–172.5°.

B. 2-Amino-3-(3-methyl-2-oxo-1H-benzimidazol-5-yl)propionic Acid Hydrochloride

The title compound is prepared by treating the product from part A with 4N HCl at reflux for 2 hours, evaporation of the volatile solvents and treating the residue with hydrogen, formaldehyde, sodium acetate and Raney nickel catalyst according to the procedure of Emerson et al., J. Am. Chem. Soc. 62, 69 (1940). Phosgene gas is then bubbled (approximately 60 ml/min) through the resulting mixture in 1N HCl (100 ml) for 1 hour to yield 2-amino-3-(3-methyl-2-oxo-1H-benzimidazol-5-yl)propionic acid hydrochloride.

EXAMPLE 5

2-Amino-3-(1,3-dimethyl-2-oxo-2Hbenzimidazol-5-yl)propionic Acid Hydrochloride A. Diethyl-2-(3-nitro-4-N-methylacetamidobenzyl)-2-acetamidomalonate Diethyl 4-nitrobenzylacetamidomalonate (10 g.) is treated with hydrogen, formaldehyde, sodium acetate and Raney nickel catalyst by the procedure of part B of Example 4 to produce the 4-methylamino product which is refluxed for 1 hour with a slight excess of acetyl chloride to produce the N-methyl-4-acetamido product. The latter product is added slowly to 20 ml of stirring $HNO_3$ (red, fuming at −15°. After stirring, the mixture is added to an ice cold saturated $NaHCO_3$ solution, and the resulting precipitate is filtered and crystallized twice from benzene.

B. 2-Amino-3-(1,3-dimethyl-2-oxo-2H-benzimidazol-5-yl)propionic Acid Hydrochloride The 2-amino-3-(1,3-dimethyl-2-oxo-2H-benzimidazol-5-yl)propionic acid hydrochloride is prepared by treating the product from part A. first with hydrogen, formaldehyde, sodium acetate and Raney nickel catalyst according to the procedure of Example 4, secondly with 10% hydrochloric acid heated to reflux for 1 hour and finally with phosgene gas for 1 hour by the procedure of part B of Example 4.

EXAMPLE 6

2-Amino-3-(3-methyl-2-oxo-1H-benzimidazol-6-yl)propionic Acid Hydrochloride

By following the procedure of Example 1 but substituting diethyl-2-(3-nitro-4-N-methylacetamidobenzyl)-2-acetamidomalonate (prepared as described in part A of Example 5) for DL-methyl-N-acetyl-3-(3-nitro-4-acetamidophenyl)-2-methylalanate, the Example 6 title compound is prepared.

EXAMPLE 7

2-Amino-2-methyl-3-(3-methyl-2-oxo-1H-benzimidazol-6-yl)propionic Acid Hydrochloride A. Methyl 2-acetamido-2-methyl-3-(3-nitro-4-N-methylacetamidophenyl)propionate Methyl 2-acetamido-2-methyl-3-(4-nitrophenyl)propionate is treated with hydrogen, formaldehyde, sodium acetate and Raney nickel catalyst by the procedure of part B of Example 4 to produce the crude 4-methylamino product which when treated with a slight excess of acetic anhydride and heated to reflux for 1 hour, yields the 4-N-methylacetamido compound. The latter product is added slowly to 20 ml of stirring $HNO_3$ (red fuming) at $-15°$. After stirring, the mixture is added to an ice cold saturated $NaHCO_3$ solution, and the resulting precipitate is filtered and recrystallized twice from benzene.

2-Amino-2-methyl-3-(3-methyl-2-oxo-1H-benzimidazol-6-yl)propionic Acid Hydrochloride 2-Amino-2-methyl-3-(-methyl-2-oxo-1H-benzimidazol-6-yl)propionic acid HCl is prepared by treating the product from part A. with 10% hydrochloric acid heated to reflux for 1 hour followed by reaction with hydrogen gas over palladium on carbon and treating the resulting mixture with phosgene gas by the method of part B of Example 4.

EXAMPLE 8

2-Amino-2-methyl-3-(3-methyl-2-oxo-1H-benzimidazol-5-yl)propionic Acid Hydrochloride Methyl 2-acetamido-2-methyl-3-(3-nitro-4-acetamidophenyl)propionate is treated with hydrogen, formaldehyde, sodium acetate and Raney nickel following the procedure of part B of Example 4 to produce 2-acetamido-2-methyl-3(3-methylamino-4-aminophenyl)propionic acid. This product is hydrolyzed with 10% HCl and cyclized with phosgene by the procedure of part B of Example 4 to yield Example 8 title compound.

EXAMPLE 9

2-Amino-2-methyl-3-(1,3-dimethyl-2-oxo-2H-benzimidazol-5-yl)propionic Acid Hydrochloride Following the procedure of Example 8 but replacing the product of part A, Example 7 for methyl-2-acetamido-2-methyl-3-(3-nitro-4-acetamidophenyl)propionate, Example 9 title compound is prepared.

EXAMPLE 10

2-Amino-3-(2-ethoxybenzimidazol-5-yl)propionic Acid

A mixture of diethyl-2-(3-nitro-4-acetamidobenzyl)-2-acetamidomalonate is held at reflux with 10% HCl for 2 hours. The resulting mixture is cooled and then treated with hydrogen (initial pressure 35 psig) on 10% palladium on charcoal catalyst at room temperature overnight. The solution is then evaporated to dryness and the residue treated with a slight excess of iminocarbonic acid diethylester following the procedure of Sandmeyer [Ber., 19, 2650 (1996)] to give Example 10 title compound.

EXAMPLE 11

2-Amino-3-(1-methyl-2-ethoxybenzimidazol-6-yl)propionic Acid

The Example 11 title compound is prepared by treating the product from part A of Example 4 with hydrogen, formaldehyde, sodium acetate and Raney nickel catalyst according to the procedure of part B of Example 4 and then treating the resulting mixture with 10% HCl held at reflux for 2 hours followed by evaporation to dryness and treatment of the residue with iminocarbonic acid diethyl ester by the procedure of Example 10.

EXAMPLE 12

2-Amino-3-(1-methyl-2-ethoxybenzimidazol-5-yl)propionic Acid

By following the procedure of Example 10 but substituting diethyl-2-(3-nitro-4-N-methylacetamidobenzyl)-2-acetamidomalonate (Example 5, part A) for diethyl-2-(3-nitro-4-acetamidobenzyl)-2-acetamidomalonate, the Example 12 title compound is prepared.

EXAMPLE 13

2-Amino-2-methyl-3-(2-ethoxybenzimidazol-5-yl)propionic Acid

By following the procedure of Example 10 but substituting methyl-2-acetamido-2-methyl-3-(3-nitro-4-acetamidophenyl)propionate for diethyl-2-(3-nitro-4-acetamidobenzyl)-2-acetamidomalonate, the Example 13 title compound is prepared.

EXAMPLE 14

2-Amino-2-methyl-3-(1-methyl-2-ethoxybenzimidazol-5-yl)propionic Acid

By following the procedure of Example 10 but substituting methyl-2-acetamido-2-methyl-3-(3-nitro-4-N-methylacetamidophenyl)propionate (Example 7, part A) for diethyl-2-(3-nitro-4-acetamidobenzyl)-2-acetamidomalonate, the Example 14 title compound is prepared.

EXAMPLE 15

2-Amino-2-methyl-3-(1-methyl-2-ethoxybenzimidazol-6-yl)propionic Acid

Methyl-2-acetamido-2-methyl-3-(3-nitro-4-acetamidophenyl)propionate is treated with hydrogen, formaldehyde, sodium acetate and Raney nickel following the procedure of Example 4 to produce the 3-methylamino product. The Example 15 title compound is prepared by following the procedure of Example 11 but substituting the 3-methylamino product [methyl-2-acetamido-2-methyl-3-(3-methylamino-4-acetamidophenyl)propionate] for methyl-2-(3-methylamino-4-acetamidobenzyl)-2-acetamidomalonate.

EXAMPLE 16

D,L-3-(Benzimidazol-2-one-5-yl)-2-methylalanine methyl ester

A mixture of the product of Example 1 (0.1 mole) is held at reflux in 1500 ml of MeOH saturated with HCl gas for 6 hours. The alcoholic solution is evaporated to yield a gum which is recrystallized from water or MeOH:ether, to yield D,L-3-(benzimidazol-2-one-5-yl)-2-methylalanine methyl ester.

EXAMPLE 17

2-Amino-3-(2-oxobenzoxazol-5-yl)propionic Acid Hydrochloride

A solution of 3-nitrotyrosine (5.0 g., 22.1 mmole) in 100 ml of acetic acid is shaken overnight with hydrogen (initial pressure 35 psi) and 10% palladium on charcoal catalyst. The suspension is filtered through a bed of diatomaceous earth and the solvent removed under vacuum. Phosgene gas is bubbled (approx. 60 ml/min) through a solution of the residue in 1N HCl (100 ml) for 1 hour. The precipitate which develops upon cooling is collected and recrystallized from methanol/ether to yield Example 17 title compound, m.p. 265° C (decomp.).

EXAMPLE 18

2-Amino-2-methyl-3-(2-oxobenzoxazol-5-yl)propionic Acid Hydrochloride

By following the procedure of Example 17 but substituting 2-amino-2-methyl-3-(3-nitro-4-hydroxyphenyl)-propionic acid for 3-nitrotyrosine, the Example 18 compound is obtained.

EXAMPLE 19

2-Amino-3-(3-methyl-2-oxo-2Hbenzoxazol-5-yl)-propionic Acid Hydrochloride

3-Nitrotyrosine (5.0 g) is refluxed with a slight excess of acetyl chloride for 1 hour. The resulting product is then esterified by contact with an excess of methanol under acidic conditions. On evaporation of the excess alcohol, the methyl ester of O,N-diacetyl-3-nitrotyrosine is recovered. Reductive alkylation of this product with hydrogen, formaldehyde, sodium acetate and Raney nickel catalyst (J. Amer. Chem. Soc., 62, 69 (1940) produces the 3-methylamino product. This product is held at reflux with 10% HCl for 2 hours, cooled, and then treated with phosgene gas by the procedure of Example 17 to produce the Example 19 title compound.

EXAMPLE 20

2-Amino-2-methyl-3-(3-methyl-2-oxo-2H-benzoxazol-5-yl)propionic acid

By following the procedure of Example 19 but substituting 3-nitro-α-methyltyrosine for 3-nitrotyrosine, the Example 20 title compound is obtained.

EXAMPLE 21

2-Amino-3-(2-oxobenzoxazol-5-yl)propionic acid methyl ester

The product from Example 17 is held for 6 hours at reflux in 1500 ml of methanol saturated with HCl gas. The alcoholic solution is evaporated to yield a product which is recrystallized from water or methanol: ether to yield the Example 21 title compound.

The present compositions encompass combinations in which the weight ratio of the decarboxylase inhibitor (A): aryl alanine (B) may be varied. A weight ratio range of (A):(B) from about 400:1 to About 1:4 is useful. A preferred (A):(B) weight ratio range is about 200:1 to about 1:2, a more preferred weight ratio is about 100:1 to about 1:1; and a weight ratio range of about 10:1 to about 1:1 is most preferred.

The composition is administered to hypertensive animals in an amount sufficient to effect the desired reduction in blood pressure. The dosage, on a daily bais may range from about 0.2 mg/kg to about 1000 mg/kg of animal body weight. This dose may be administered in a single unit or, as is more generally done, the dose is divided into a number of smaller units given in the period of a day.

The compositions may be administered orally or parenterally. The compositions are provided in suitable dosage forms which are prepared in a conventional manner and are generally combined with suitable carriers, diluents, stabilizers, dyes etc. For oral administration, suitable dosage forms include tablets, capsules, liquid mixtures and the like — for parenteral administration suitable dosage forms include liquid compositions, such as solutions, suspensions or emulsions and the like.

Following are examples illustrating dosage forms:

| TABLET FORMULATION | |
|---|---|
| S-3-(benzimidazol-5-yl)-2-methyl alanine dihydrochloride | 20 mg |
| Carbidopa | 5 mg |
| Calcium Phosphate | 100 mg |
| Lactose | 50 mg |
| Starch | 12 mg |
| Magnesium Stearate | 1 mg |
| CAPSULE FORMULATION | |
| 3-(Benzoxazol-2-one-5-yl) alanine hydrochloride | 125 mg |
| Carbidopa | 125 mg |
| Lactose, U.S.P. | 93 mg |
| Talc | 7 mg |
| INJECTABLE SOLUTION | |
| 3-(Benzimidazol-5-yl)- alaine hydrochloride | 1.0 mg |
| Carbidopa | 10.0 mg |
| Distilled Water q.s.   1 ml | |
| LIQUID SUSPENSION FORMULATION | |
| 3-(Benzimidazol-2-one-5-yl) 2-methylalanine hydrochloride | 10 g |
| Carbidopa | 500 g |
| Veegum H.V. | 300 g |
| Methyl Paraben | 50 g |
| Kaolin | 50 g |
| Glycerine | 500 g |
| Water q.s.   1 liter | |

The compositions of the present invention are administered to hypertensive animals to produce a hypotensive effect i.e. reduction in blood pressure. The decarboxylase inhibitor component is known to have no appreciable antihypertensive (hypotensive) activity. The arylalanines include compounds which have some antihypertensive activity and some that have no such activity. Where the arylalanine has some hypotensive activity, the combination with the decarboxylase inhibitor enhances this activity. Where the arylalanine has no measurable antihypertensive effect, the combination with the decarboxylase inhibitor produce a measurable hypotensive effect.

The antihypertensive activity or enhancement of activity is demonstrated in vivo in spontaneously hypertensive (SH) rats. The procedure used is as follows:

The test animals were conscious, male, SH rats weighing about 290 to about 340 grams. The arterial blood pressure was measured by a direct technique involving cannulation of the caudal artery. Initial blood pressure was recorded. The decarboxylase inhibitor was then administered intraperitoneally (i.p.) and about 5 minutes later an arylalanine compound was administered (i.p.). The blood pressure was then continuously recorded at half hour intervals for 24 hours.

The effect on blood pressure of the decarboxylase inhibitor and the arylalanine alone was also determined using this method.

The test results obtained from this evaluation were reported in terms of antihypertensive activity i.e. extent of blood pressure reduction effected. Data for representative compounds and compositions of the present invention are presented in the following table:

Table I

| Antihypertensive Effect Per SH Rat Evaluation | | | |
|---|---|---|---|
| Test No | Composition | Dose (mg/kg) | Antihypertensive Activity |
| 1 | Carbidopa | 25 | In. |
| 2 | L-3-(benzimidazol-5-yl) 2-methylalanine . HCl | 80 | Sl. Act. |
| 3 | L-3-(benzimidazol-5-yl)-2-methylalanine . HCl + Carbidopa | 0.3  25 | Mod. Act. |
| 4 | D,L-3-(benzimidazol-5-yl)-alanine . HCl | 80 | Sl. Act./Mod. Act. |
| 5 | D,L-3-(benzimidazol-5-yl)-alanine . HCl + Carbidopa | 1.25  25 | Mod. Act./Pro. Act. |
| 6 | 3-(benzimidazol-2-one-5-yl)-2-methylalanine . HCl | 20 | Mod. Act. |
| 7 | 3-(benzimidazol-2-one-5-yl)-2-methylalanine . HCl + Carbidopa | 1.25  25 | Act. |
| 8 | L-3-(benzoxazol-2-one-5-yl) alanine . HCl | 80 | In. |
| 9 | L-3-(benzoxazol-2-one 5-yl)-alanine . HCl + Carbidopa | 1.25  25 | Lowered Arterial Pressure |

[1]In each test, Carbidopa was dissolved in 1N HCl while the aryl alanine was dissolved in water.
[2]In. = substantially inactive
Sl. Act. = Slightly Active
Act. = Active
Mod. Act. = Moderately Active
Pro. Act. = Pronounced Activity The data in Table I demonstrates the unexpectedly enhanced antihypertensive activity of the compositions of the present invention. At 25 mg/kg, carbidopa, the decarboxylase inhibitor, has substantially no antihypertensive activity. With representative arylalanines that have some antihypertensive activity (Test 2,4 & 6), the inactive carbidopa unexpectedly improves the antihypertensive effectiveness of these arylalanines (Test 3, 5 & 7). With an arylalanine showing substantially no antihypertensive activity (Test 8), the combination with inactive carbidopa shows activity (Test 9).

While the antihypertensive evaluation involved intraperitoneal administration of the test compounds individually, the results are indicative of the effect which is obtained by oral or parenteral administration of the decarboxylase inhibitor and arylalanine either individually and simultaneously or as a combination e.g. as a mixture. Another embodiment of the invention is a method of treating hypertension in hypertensive animals by thus administering a hypotensive amount of the present compositions.

The term animals includes humans.

Claims to the invention follow.

What is claimed is:

1. A pharmaceutical composition for treating hypertension comprising
A. a decarboxylase inhibitor compound having the formula

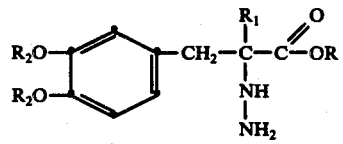

wherein R, $R_1$, $R_2$ and $R_3$ are independently selected from hydrogen and $C_1$-$C_4$ alkyl, and pharmaceutically acceptable salts thereof and
B. an arylalanine having the formula:

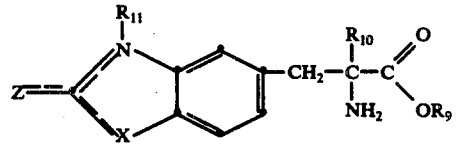

wherein
$R_9$, $R_{10}$, and $R_{11}$ are independently selected from hydrogen and $C_1$-$C_4$ alkyl,
X is O
Z is = O or —O—$R_{13}$ wherein $R_{13}$ is selected from hydrogen or $C_1$-$C_4$ alkyl, and pharmaceutically acceptable salts thereof in an effective amount.

2. The composition of claim 1 wherein said decarboxylase inhibitor has the formula:

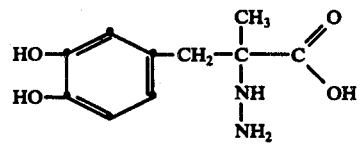

and pharmaceutically acceptable salts thereof.

3. The composition of claim 2 wherein said decarboxylase inhibitor is the L-isomer.

4. The composition of claim 3 wherein said arylalanine is the
2. compound having the formula:

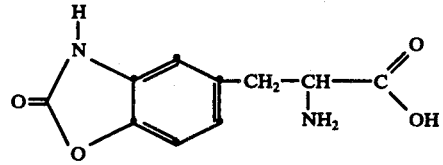

and pharmaceutically acceptable salts thereof.

5. A method of treating hypertension in hypertensive animals which comprises administering an effective amount of the claim 1 composition.

* * * * *